United States Patent [19]

Valaskovic et al.

[11] Patent Number: 5,788,166

[45] Date of Patent: Aug. 4, 1998

[54] ELECTROSPRAY IONIZATION SOURCE AND METHOD OF USING THE SAME

[75] Inventors: Gary A. Valaskovic; Fred W. McLafferty, both of Ithaca, N.Y.

[73] Assignee: Cornell Research Foundation, Inc., Ithaca, N.Y.

[21] Appl. No.: 703,644

[22] Filed: Aug. 27, 1996

[51] Int. Cl.[6] .................................................. B05B 5/057
[52] U.S. Cl. .................................................. 239/708; 239/690
[58] Field of Search .................................. 239/690, 708, 239/602; 250/288, 281

[56] References Cited

U.S. PATENT DOCUMENTS

| | | |
|---|---|---|
| 4,705,616 | 11/1987 | Andresen et al. |
| 4,997,537 | 3/1991 | Karger et al. |
| 5,089,106 | 2/1992 | Karger et al. |
| 5,098,539 | 3/1992 | Shieh |
| 5,115,131 | 5/1992 | Jorgenson et al. |
| 5,120,414 | 6/1992 | Carson et al. |
| 5,306,412 | 4/1994 | Whitehouse et al. |
| 5,306,910 | 4/1994 | Jarrell et al. |
| 5,349,186 | 9/1994 | Ikonomou et al. |
| 5,382,794 | 1/1995 | Downey et al. |
| 5,393,975 | 2/1995 | Hail et al. |
| 5,401,963 | 3/1995 | Sittler |
| 5,415,747 | 5/1995 | Holloway |
| 5,421,980 | 6/1995 | Guttman |
| 5,423,964 | 6/1995 | Smith et al. |
| 5,468,452 | 11/1995 | Hagiwara |
| 5,477,046 | 12/1995 | Dietrich et al. |
| 5,504,329 | 4/1996 | Mann et al. |
| 5,505,832 | 4/1996 | Laukien et al. |
| 5,572,023 | 11/1996 | Caprioli .................... 250/288 |
| 5,608,217 | 3/1997 | Franzen et al. ............ 250/288 |

OTHER PUBLICATIONS

Guan et al., "High Sensitivity Protein Sequencing with ESI–FTMS", 1995 ASMS Abstract, Apr. 1995.
Chowdhury, Swapan K. et al., "Method for the Electrospray Ionization of Highly Conductive Aqueous Solutions", Anal. Chem. 1991, 63, pp. 1660–1662.
Emmett, Mark R. et al., "Micro–Electrospray Mass Spectrometry: Ultra–High–Sensitivity Analysis of Peptides and Proteins", J. Am. Soc. Mass Spectrom. 1994, pp. 605–613.
Gale, David C. et al., "Small Volume and Low Flow–Rate Electrospray Ionization Mass Spectrometry of Aqueous Samples", Rapid Communications in Mass Spectrometry, vol. 7, pp. 1017–1020, 1993.
Kriger, M. Scott et al., "Durable Gold–Coated Fused Silica Capillaries for Use in Electrospray Mass Spectrometry", Analytical Chemistry, vol. 67, No. 2, Jan. 15, 1995, pp. 385–389.
Wilm, M.S. et al., "Electrospray and Taylor–Cone Theory, Dole's Beam of Macromolecules at Last?", J. Mass Spectrom. Ion Processes 136, 1994, pp. 167–180.

*Primary Examiner*—Lesley D. Morris
*Attorney, Agent, or Firm*—Jones, Tullar & Cooper

[57] ABSTRACT

An ultra-low flow rate electrospray ionization (ESI) source provides flow rates in the range of 1.0 nL/min or less. The source is comprised of a needle which is fabricated by laser-heated pulling of fused-silica tubing, followed by chemical etching and surface metallization. The pulling results in formation of a slowly tapering capillary within the needle which tapers to a tip having a very small inner diameter. The etching process sharpens the outer wall of the needle to a very sharp tip, and the combination of these parameters results in the ultra-low flow rate capability. After a metal electrical contact is formed on the exterior wall of the needle, an electrically insulating overcoating is preferably deposited thereon which locks the contact in place, thereby greatly increasing needle life, and also restricting the electrical contact point to the very tip of the needle. Although the use of the ultra-low flow rate ESI sources increases sensitivity to sampling errors, a mechanism is also provided to minimize one primary source of such errors, evaporation induced hydrodynamic flow, in capillary electrophoresis (CE). An injection system is provided which enables a retractable droplet of buffer solvent to be positioned in contact with the tip end of the ESI needle during sample loading. This prevents evaporation from the tip end, thereby eliminating hydrodynamic flow into the distal end of the capillary column used in the CE process.

18 Claims, 5 Drawing Sheets

ELECTROSPRAY IONIZATION SOURCE AND METHOD OF USING THE SAME

BACKGROUND OF THE INVENTION

The present invention relates in general to an electrospray ionization source for mass spectrometry, and a method of using the same.

Electrospray ionization (ESI) is a technique whereby molecules in solutions are transformed to ions in the gas phase. ESI has been highly successful in the ionization, and subsequent analysis by mass spectrometry (MS), of large biological molecules, such as proteins and DNA. Minimizing sample volume is important in bioanalytical chemistry and biomedicine where there is increasing attention on chemical analysis at the level of a single cell or single nerve synapse. For example, subattomole sensitivity has been demonstrated with capillary electrophoresis (CE) but with low chemical specificity. Integration of CE with electrospray ionization MS, especially with Fourier transform (FT) MS, improves specificity dramatically; recent reports demonstrate hemoglobin mass spectra from 10 red blood cells (5 fmol, FTMS) and peptide mass spectra of limited mass range from 0.3 fmol samples (consuming only ~10 amol). The sample requirements for such ESI-MS systems (50 fmole achieved for conventional ESI-MS) have been substantially lowered by the discovery that reducing ESI sample flow rates from 1 μL/min to as low as 25 nL/min yields a far smaller reduction in the signal-to-noise ratio.

To obtain these low flow rates, the ESI glass "needles" employed to supply the solution to be ionized must be specially fabricated. One type of needle is fabricated from fused-silica capillary tubing with an inner diameter of between 5 and 250 μm in which a sharp tip is formed by etching or grinding. These needles can utilize much smaller and observable sample volumes. A second type of needle is formed by heat softening 0.5–1.0 mm inner diameter glass capillary tubing, and pulling it down to form tips of 1–3 μm inner diameter. The much smaller droplets from these yield a stable spray at lower flow rates of between 25 and 50 nL/min, with improved desolvation and ionization efficiency. Until now, ESI sources have yet to be devised which can provide ultra-low flow rates of less than 25 nL/min.

Current ESI sources also suffer from durability problems. These sources are generally constructed from either small metal tubes (e.g., a steel syringe needle) or dielectric tubing (e.g., glass, fused silica or polymer tubing). ESI tips constructed from insulating materials require a means of making electrical contact with the analyte solution. This has been accomplished in three ways: making a direct electric contact with the solution from a position remote to the ESI tip, supporting the dielectric tip inside a secondary metal tube that contacts the liquid as it exits the dielectric tube, and applying thin metal films directly onto the dielectric tubing. The latter method has been the electrical contact of choice for low flow rate ESI devices, especially when combined with CE.

To make electrical contacts for the needle tips, it is desirable to apply a film of an inert electrical conductive material, such as gold or platinum, to the ESI tips because they are electrochemically stable and thus will not be dissolved in the ESI analyte solution. Unfortunately, because of their relatively inert nature, such metals often show poor adhesion to the substrate materials which reduces ESI stability and eventually leads to ESI tip failure. As analyte is sprayed from the tip, the metal coating can rapidly deteriorate by flaking or peeling off of the ESI tip surface. A previous solution to this problem has been to improve the adhesion of the metal coating to the substrate by the application of an interlayer material that adheres to both the metal and the substrate. Interlayer materials, such as chromium or sulfur containing silanes, are known to markedly improve the adhesion of gold to glass in silica substrates. Unfortunately, such interlayer materials are subject to chemical attack, either by dissolving in the case of chromium or bond cleavage in the case of silanes, under certain solution conditions. A need therefore still exists for a better solution to this durability problem.

The use of ultra-low flow rate ESI sources in CE presents yet another problem. In particular, the use of such low flow rates results in an increased sensitivity to systematic errors. One previously unreported source of systematic error is caused by induced (hydrodynamic) flow in sheathless CE electrospray. In particular, hydrodynamic flow is caused by the ESI tip being exposed to the atmosphere which results in evaporation of buffer solvent, thereby inducing flow inside the column. This induced flow can cause an under estimation of injection size for quantitative electrokinetic sampling by as much as 50%. For such an apparatus, sample introduction by electrokinetic injection into the head of the capillary column is favored because of its experimental simplicity, reproducability and small injection volume. However, the foregoing source of serious errors in the sample size measurement must be overcome if ultra-low flow rate ESI-CE is to be practical.

SUMMARY OF THE INVENTION

To address the foregoing problems, an ESI source is provided which can supply ultra-low flow rates of less than 1.0 nL/min. To achieve such a low flow rate, the ESI source (needle) employs a novel tip shape which combines a plurality of physical characteristics. The first of these characteristics is the provision of a small tip inner diameter to limit droplet size. A capillary leading to the tip is also provided which has an elongated, slowly tapering portion leading to the tip to limit the flow of the liquid inside the tube because of viscous resistance to flow. The outside wall of the needle tapers toward the tip to a sharp point with a very thin tip wall, thereby resulting in a very-high electric field to support low flow rates. The tapered wall of the needle also supports a high electric field and provides structural integrity. The result of combining these physical characteristics is that the needle can supply a sample at a flow rate of less than 0.25 nL/min, which is two orders of magnitude lower than was previously achievable by using tips with only the small inner diameter.

Preferably, the needle is formed from a suitable material, such as fused silica, which can be pulled and etched to obtain the desired characteristics. A small inner diameter tube is first heated and pulled to form the small tip inner diameter and the slowly tapering capillary. Next, etching is employed to form the tapered outer wall and sharp point at the tip of the needle. A metal electrical contact layer is then formed on or applied to the outer wall of the needle adjacent the tip for supplying an ESI potential thereto.

To improve the durability of the ESI source, an electrically insulating, durable overcoating is formed over the metal electrical contact layer on the tip. The overcoating can be any suitable electrically insulating material, such as a polymer or an oxide, and is applied using any suitable conventional technique, such as dipping, spraying or any type of deposition technique. The resulting overcoating is extremely hard, electrochemically stable, chemically resistant to attack by most acids and bases and electrically insulating. The overcoating locks the underlying conductive metal layer into place, thereby greatly enhancing durability of the metal contact even though adhesion is not improved by the process. The use of an electrically insulating material also limits electrical contact between the metal coating and the electrosprayed solution to a small ring at the very tip of the ESI needle, which further enhances electrospray stability.

In the use of the ultra-low flow rate ESI source in CE, for example, the sampling errors caused by evaporation induced hydrodynamic flow are eliminated by temporarily immersing the needle tip in buffer solvent during sample loading into a capillary column. This procedure improves sampling reproducability and accuracy, and also eliminates the introduction of air bubbles into the column during the sampling process. Preferably, this is accomplished by positioning a tube adjacent the needle tip which is employed to supply a retractable droplet of buffer solvent to the tip during sample loading. Alternatively, the retractable droplet can be employed to control sample loading into the column using the evaporation induced flow where this flow can be calculated or measured.

BRIEF DESCRIPTION OF THE DRAWINGS

The features and advantages of the present invention will become apparent from the following detailed description of the preferred embodiments thereof, taken in conjunction with the accompanying drawings, in which:

FIG. 4B being a light photomicrograph of the needle after etching; and FIG. 4C being a high-resolution scanning electron microscopy (SEM) photomicrograph of a 2.3 μm ID needle tip after etching;

DETAILED DESCRIPTION OF THE PREFERRED EMBODIMENTS

Figure 1:
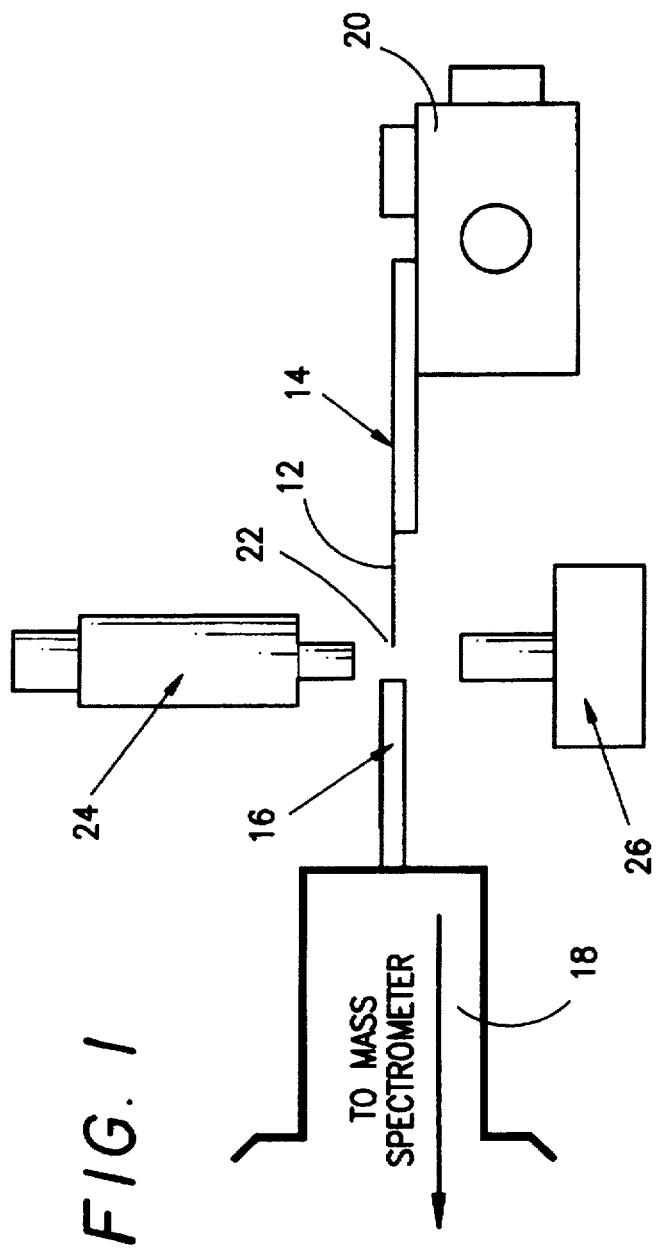
FIG. 1 is a schematic illustration of an ESI inlet system with which an ESI needle constructed in accordance with the present invention may be used.

Ultra-low flow rate ESI needles were constructed in accordance with a preferred embodiment of the invention as described in detail below, and experiments were conducted to test their flow rate capabilities. FIG. 1 illustrates an ESI inlet system 10 which was employed in these experiments. As is conventional, an ESI source, specifically a needle 12, is positioned on a mount 14 for spraying ions into a capillary inlet 16 of a mass spectrometer 18 for analysis.

The ESI needle 12 is preferably formed from fused silica in a manner to be described later, and is glued onto the end of the mount 14, which in turn is attached to an X, Y, Z stage 20 for fine positioning with respect to the capillary inlet 16. Flow through a tip 22 of the ESI needle 12 is monitored by a conventional transmitted light microscope 24 with assistance from an illuminator 26. The optimum distance between the ESI tip 22 and the capillary inlet 16 is approximately 0.25–1.5 mm.

Figure 2:
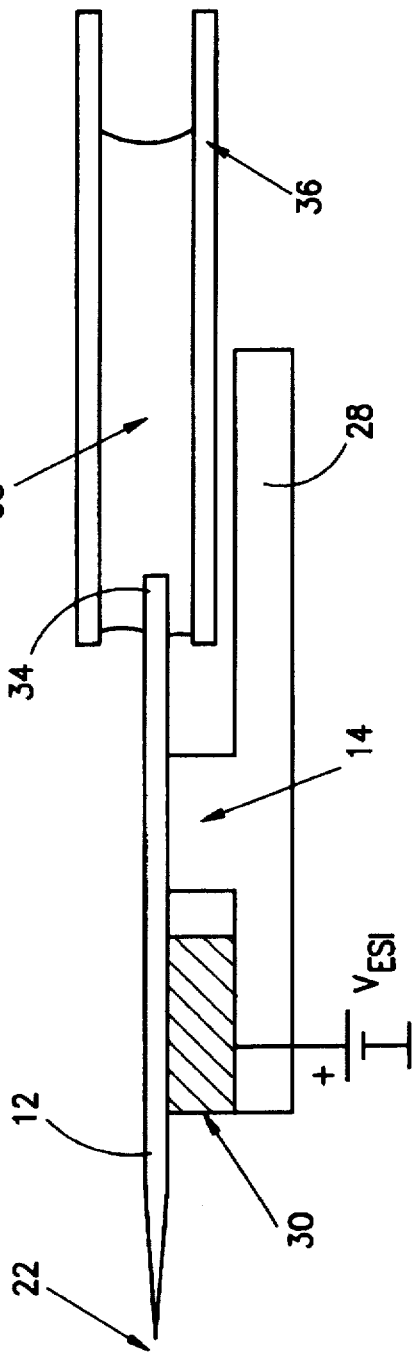
FIG. 2 is a schematic illustration showing the details of a mount for the ESI needle.

As illustrated in FIG. 2, the needle mount 14 includes an insulating portion 28, which is preferably made from glass, and an electrical contact 30 (preferably made from copper) that is positioned on the end of the insulating portion 28 in contact with another electrical contact (not shown in FIG. 2) on the ESI needle 12. A positive or negative tip-inlet potential, typically 600–1300 V, is applied from a power supply 32 through the copper contact 30 to the needle tip 22 for effecting electrospray into the capillary inlet 16. To deliver analyte to a distal end 34 of the ESI needle 12, a capillary 36 of glass or plastic is provided which is filled with the analyte 38.

Figure 3:
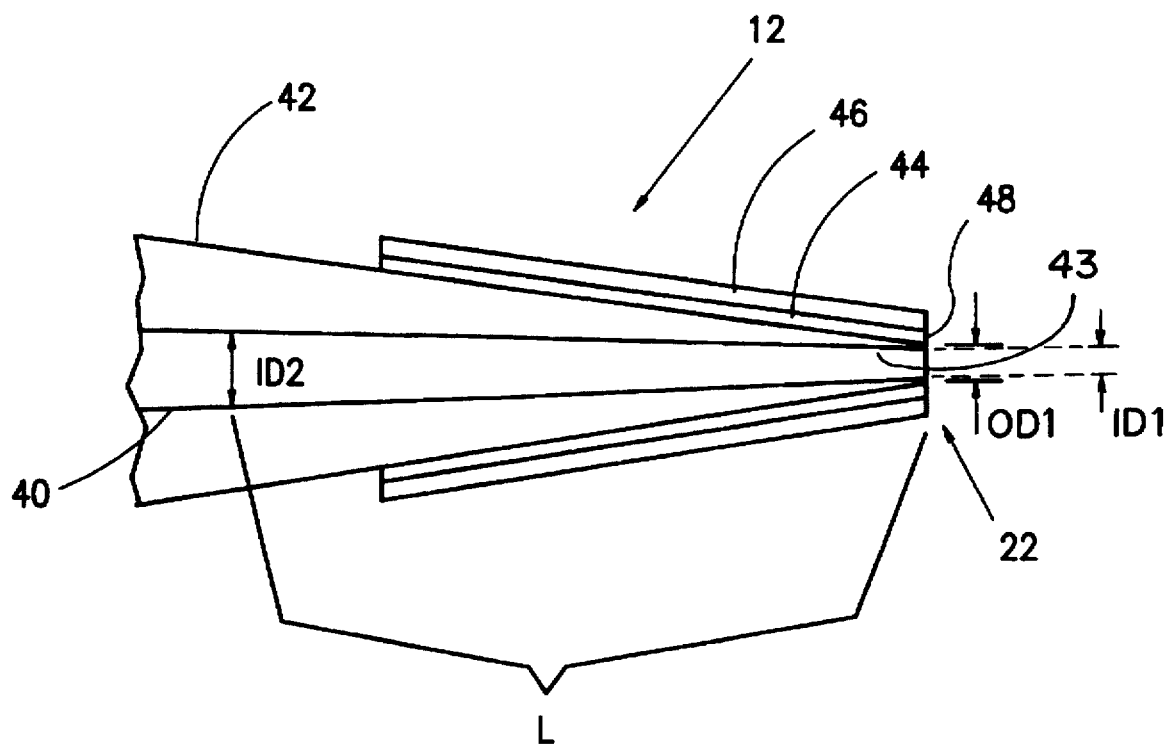
FIG. 3 is a schematic illustration showing the cross-section of the ESI needle in detail.

FIG. 3 illustrates the details of the ESI needle tip 22, many of which are crucial to its ultra-low flow rate capabilities. The design of the ESI needle 12 meets the following three major requirements. First, apparatus volume is minimized to enhance analytical sensitivity and the flow rate is low enough for optimal MS acquisition of that volume. Second, stable ESI is maintained at the lowest possible flow rate of less than 1.0 nL/min. Finally, efficiency of sample ionization and ion transmission into the mass spectrometer 18 is maximized.

To achieve these requirements, the ESI needle 12 has the following characteristics. First, the inner diameter of a capillary 40 within the ESI needle 12 is made as small as possible along its length leading up to the tip 22. Preferably, the inner diameter of the capillary 40 at the tip 22, labelled ID1, should be less than approximately 7 μm, preferably 3–5 μm, to limit droplet size. A very gradual taper is preferably formed along a length L of the capillary 40, where L is at least approximately 0.25–3.0 mm, so that at the distance L from the tip 22, the inner diameter ID2 of the capillary 40 is somewhat larger than the inner diameter ID1 at the tip 22. ID2 should be no more than approximately 10 μm greater than ID1, and preferably, ID2 is approximately 5 μm or less greater than ID1. The slowly tapering inner diameter of capillary 40 provides capillary flow towards the tip 22, while the small inner diameter of the capillary 40 enables it to handle very small (less than or equal to 1 nL) samples and to limit viscous flow.

It should be noted that the use of a small inner diameter for the tip 22 is not enough in and of itself to provide ultra-low flow rates on the order of 1 nL/min or less. In previous ESI devices, the use of small inner diameters alone has only resulted in the reduction of flow rates to as low as 25 nL/min. To achieve ultra-low flow rates in the 1 nL/min or less range, the small tip inner diameter must be combined with the gradually tapering capillary 40, as well as the following additional characteristics. In particular, the tip 22 is made very sharp by tapering an outer wall 42 of the tip 12 down to a sharp point at the tip 22 where the thickness of a tip wall 43 is extremely thin (approximately 50–100 nm or less), such that the outer diameter OD1 of the needle tip 22 is no more than approximately 10% greater than its inner diameter ID1. The extremely thin tip wall 43 and taper of the outer wall 42 leading up to the tip wall 43 results in generation of a very high electric field when power is supplied to a gold contact layer 44 on the outer wall 42, and the taper also provides structural integrity for the ESI needle 12.

Another feature of the needle 12 which greatly increases its durability is the provision of an insulating coating 46 over the gold contact layer 44. The purpose of the overcoating 46 is to "lock" the gold contact layer 44 in place, thereby greatly increasing its lifetime. Without the overcoating 46, the gold contact layer 44 is highly susceptible to deterioration by electrical discharge, and can only last approximately 15 to 30 minutes with continuous ESI. This problem is due in large part to the poor adhesion of the gold contact layer 44 resulting from its very small optimum thickness of approximately 100 nm or less.

Preferably, the overcoating 46 is made from a hard insulating material, such as $SiO_x$ (mixed SiO and $SiO_2$) or a polymer, and preferably has a thickness of approximately 10–50 nm. The overcoat 46 can be applied using any conventional deposition technique, such as thermal evaporation, but it is important that SiO evaporation conditions be carefully controlled so that a small ring 48 of the gold contact layer 44 is left exposed at the end of the ESI needle tip 22. In experiments, when the angle between the SiO evaporation (point) source and the capillary tip end was decreased from approximately 120° to 90°, and the $SiO_x$ thickness was increased to greater than 50 nm, the electrospray was more difficult to start, with mechanical abrasion or arcs as effective initiators in some cases; apparently too little of the gold contact layer 44 was left exposed. In other experiments on an $SiO_x$ overcoated ESI needle, the tip lifetimes were increased to between one and two hours. In addition to substantially increasing mechanical and chemical durability of the needle 12, the overcoating 46 also, by limiting the area of electrical contact to the exposed ring 48 at the tip 22, minimizes the time of the analyte solution with the electrode, thus minimizing electrochemical processes.

Figure 4A:
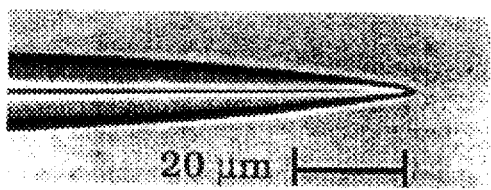
FIGS. 4A–4C are photomicrographs of an ESI needle shown during various phases of fabrication with FIG. 4A being a light photomicrograph of a needle formed from 5 μm ID tubing after pulling.
Figure 4B:
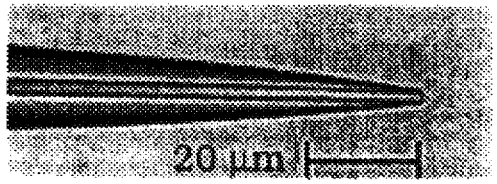
Figure 4C:
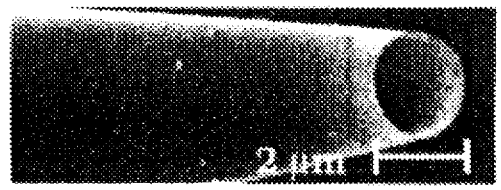

FIGS. 4A–4C are photomicrographs showing an ESI needle constructed in accordance with the preferred embodiment of the present invention. For ESI tip preparation, short lengths of small bore fused silica capillary tubing having inner diameters in the 5–20 μm range, and outer diameters of approximately 150 μm, are mounted in a modified micropipet puller. After being heated with a laser, the tubing was pulled until the tip ID is 3 μm or less. The pulling operation actually separates the tube into two needles.

FIG. 4A shows an ESI needle after it has been pulled from 5 μm ID tubing. The sharp needle tip must next be formed by etching the needle in hydrofluoric acid (HF) until a tip end wall thickness of approximately 50–100 nm or less is achieved. FIGS. 4B and 4C illustrate a sharp needle tip which is obtained after the etching process.

Using the foregoing fabrication process, the following needle characteristics listed in Table 1 were obtained with tubes of three different IDs. It should be noted that the capacity listed in the Table 1 is for 1 cm length needles.

TABLE 1

| Tube ID | Etching Time | Tip ID | Capacity | ESI Flow |
|---|---|---|---|---|
| 20 m | 60 S | 6 μm | 3 nL | 7–20 nL/min |
| 20 | 30 | 2–3 | 3 | 2–14 |
| 10 | 30 | 2–3 | 0.8 | 1–7 |
| 5 | 30 | 2 | 0.2 | 0.1–1.5 |

Further experiments have confirmed that the tip inner diameter ID1 should be no larger than approximately 7 μm, and preferably should be approximately 3–5 μm to provide a wide range of flow rates.

Figure 5:
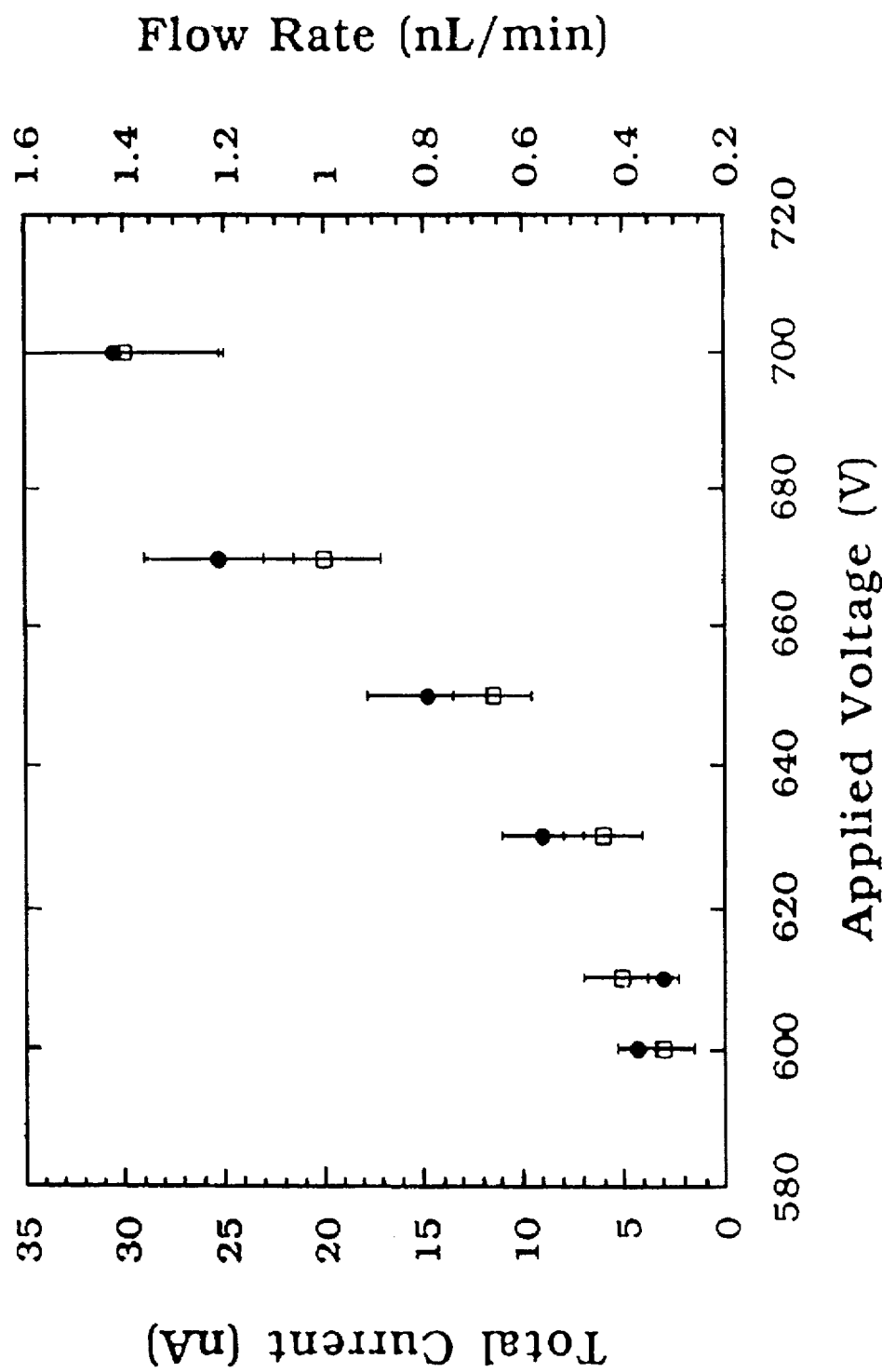
FIG. 5 is a graph illustrating the total spray current and flow rate as a function of voltage for an ESI needle constructed in accordance with the preferred embodiment of the present invention having a 2 μm ID tip, where the squares in the graph plot the total spray current and the circles plot the flow rate.

The foregoing tip parameters and operational characteristics were obtained using the system illustrated in FIGS. 1 and 2. To initiate sample flow, an electrical potential is applied by the power supply 32 to the gold contact at the needle tip 22. At a fixed potential between the tip 22 and the capillary inlet 16, decreasing the distance between the two increases the flow rate, with the upper limit in flow rate determined by the onset of corona discharge. The flow rate and total spray current are also determined by the applied voltages as illustrated in the graph of FIG. 5. (The flow rate is plotted by the circles in FIG. 5, while the total spray current is plotted by the squares.) The flow rates shown in FIG. 5 were measured by the duration or the spray current from a completely filled needle without the capillary reservoir 36.

In the system illustrated in FIGS. 1 and 2, electrostatic flow is induced in the needle 12 when the electrospray potential, $V_{ESI}$ is applied. It should be understood, however, that the ultra-low flow rates can also be obtained using other types of flow inducing mechanisms, including electroosmotic flow (EOF) in which a potential is applied across a capillary column as is commonly used in CE systems, as well as pressure assisted flow.

As discussed previously, the lowest spray rate reported for prior art ESI needles is 25 nL/min. Table 1 and FIG. 5 clearly illustrate that a spray rate two orders of magnitude lower than this is achieved with needles having a similar tip size to those employed in the prior art, but combined with the other physical characteristics in accordance with the preferred embodiment of the present invention. This appears to be due mainly to viscous flow in the small bore capillary 40; note that the flow reduction in Table 1 is more dependent on the needle capillary ID2 than on the tip ID1.

An unexpected advantage of ultra-low flow rate ESI was shown by the spectrum of single stranded DNA $T_{60}$, which exhibits little fragmentation as well as good signal to noise ratio. In contrast, the normal ESI spectrum shows substantial fragmentation. During electrospray, the capillary inlet 16 is heated to aid in droplet desolvation. With its far lower flow rate, ultra-low flow rate ESI requires a capillary heating wattage 25–50% less than that normally used, which is consistent with the decreased dissociation.

Other experiments with ESI needles constructed in accordance with the present invention indicate that an unexpectedly high signal to noise ratio (400:1), high resolving power ($>10^5$), and mass accuracy (e.g., 12,359.3 Da theory, 12,359.2 Da expt.) is maintained even though the analyte delivery rate is 1/3000 of that employed with conventional ESI. Thus, the spectrum quality obtained with conventional ESI on a given mass spectrometer should be duplicated using ultra-low flow rate ESI in accordance with the present invention. This is particularly significant for studies where sample size is severely limited.

Another particularly promising use for ultra-low flow rate ESI is with capillary electrophoresis (CE) because of its spray stability at low flow rates. However, the ultra-low flow rates greatly increase sensitivity to a notable source of systematic error in an electrokinetic injection system for a CE/ESI interface which is caused by induced hydrodynamic flow resulting from evaporation of buffer solvent from the ESI needle tip. The resulting induced hydrodynamic flow can be of such a magnitude as compared to the ultra-low flow rates provided by the ultra-low flow rate ESI needles, that substantial errors in sample volume measurements are made.

Figure 6:
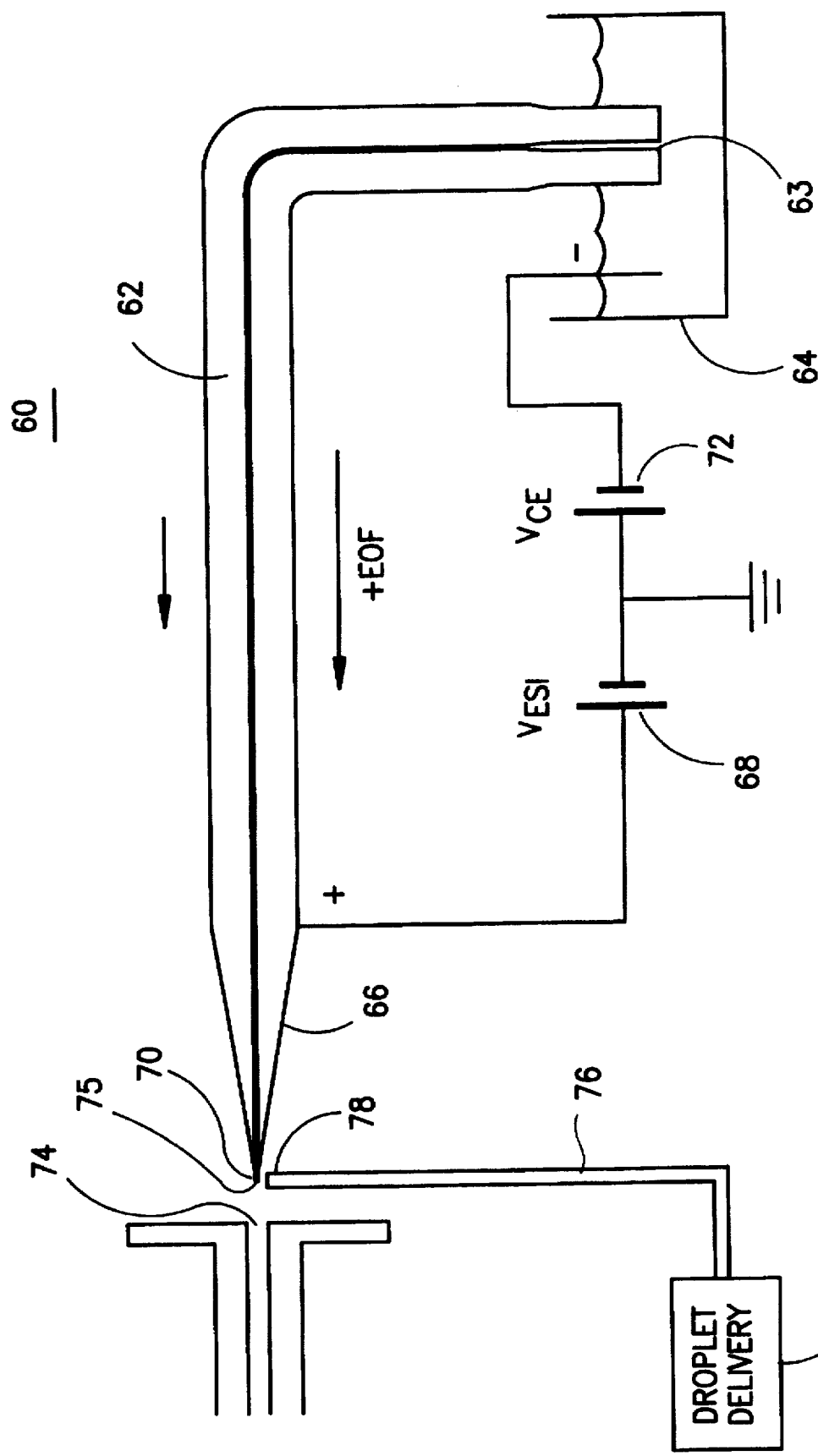
FIG. 6 is a schematic illustration of a sheathless CE-ESI interface which is employed with another preferred embodiment of the present invention.

FIG. 6 illustrates a CE/ESI interface 60 which is employed to overcome this problem. The interface 60 includes, as is conventional, a capillary column 62 having a distal end 63 immersed in a source 64 of buffer or sample for supplying the same to an integral ESI needle 66, such as one constructed in accordance with the present invention as illustrated in FIG. 3. A first voltage source 68, $V_{ESI}$, is provided for supplying an electrospray voltage of between 0.5 and 2 kV to a tip 70 of the ESI needle 66. A second power supply 72, $V_{CE}$, is provided for applying a negative potential of between 1 and 5 kV across the capillary column 62 to effect electrophoresis. The ions generated by the ESI needle 66 in response to the induced capillary flow are injected into a mass spectrometer inlet 74.

Because an open end 75 of the tip 70 is exposed to the atmosphere, evaporation of buffer solvent therefrom will occur, thereby inducing flow within the capillary column 62. This flow can cause a significant underestimation of sample size for quantitative electrokinetic sampling by as much as 50%. To eliminate this problem, the present invention provides a means for immersing the exposed tip 70 in buffer solvent or other suitable liquid during sample loading. In particular, a tube 76, preferably made from polyethylene, is positioned with an open end 78 thereof directly adjacent the needle tip 70. A droplet delivery device or system 80 is provided for retractably supplying a single 2–4 mm diameter droplet of buffer solvent or other suitable liquid to the tube end 78 so that the droplet will block off the open end 75 of the needle tip 70, thereby preventing evaporation of buffer solvent therefrom. The droplet delivery device or system 80 can be any suitable means for supplying the droplet, such as a manually operated syringe pump or an automatic computer controlled dispensing device, for example.

In operation of the system 60, the open end 75 of the needle tip 70 is blocked by the droplet during sample loading into the distal end 63 of the capillary column 62, to ensure that an evaporative flow component will not be added to the EOF induced capillary flow that will cause an inaccurate sample measurement. Once the sample is loaded into the capillary column 62, the blocking droplet is retracted, and the electrospray/electrophoresis process is begun by increasing the voltages of the ESI and CE power supplies 68 and 72. Another advantage of employing the droplet to block the needle tip 70 is that it eliminates the introduction of air bubbles into the capillary column 62 during the sampling process.

To determine the effect of the evaporatively induced flow on sampling, injections into the distal end 63 of the column 62 were performed with the ESI tip 70 exposed to air and immersed in buffer with the CE injection voltages both on and off, followed by CE/ESI/MS. The results of these experiments confirmed that when all voltages are off and the tip 70 is exposed to air, sample is nevertheless injected into the column 62 from the sample source 64. Conversely, when the tip 70 was covered with the buffer droplet, active injection only occurred when voltage was applied by the CE power supply 72 to the column 62, thereby inducing electrokinetic injection.

An evaporative mechanism is further supported by the direct observation of the meniscus movement by light microscopy. When ultra-low flow rate ESI-CE columns were filled with buffer by capillary action and the buffer reservoir was then removed from the distal end of the column, the meniscus consistently moved toward the tip at rates of less than 0.5 pL/s to as high as 5 pL/s. Movement was towards the tip because the narrowing taper of the capillary column at the tip end draws liquid to the tip end. As soon as the tip is immersed in the buffer droplet, the meniscus ceased to move toward the tip end, and almost immediately began to move toward the distal end of the column, although at a much reduced rate; the column is then filling from the tip end by capillary action. The rate of evaporative loss for one column employed in the experiments was directly measured by light microscopy to be 4 pL/s, so that a 5 second injection with voltages at ground would yield approximately 20 pL samples. The rate of evaporative loss is a complex function of ambient humidity, solution viscosity, condition of the capillary wall, capillary length, capillary ID, tip ID, and the shape of the taper. Without the buffer droplet covering the tip, there is also a strong tendency to introduce air bubbles into the column during the sampling procedure; the tendency for air bubble formation increasing with the amount of time that the distal end is exposed to the air. When the tip is immersed in the buffer droplet, the distal end of the column can be left exposed to the air for long periods of time without fear of bubble introduction.

It should be stressed that evaporative loss, and flow, occurs in columns that do not have tapered inside diameters as well; although if exposed at both ends, the evaporation occurs symmetrically from each end. This still results in sampling bias because, when immersed in the sample vial, evaporation will occur from the exposed end, again inducing capillary flow.

It should also be noted that if the evaporative loss can be accurately measured, and is reproducible for a given column, then it could also be used as a quantitative hydrodynamic injection scheme itself. In this case, the system 60 is employed in the following alternative manner. First, the tip 70 is covered with the retractable droplet of buffer solvent, while the distal end 63 of the capillary column 62 is inserted into the sample source 64. Then, the droplet is retracted, thereby exposing the tip 70 to the ambient atmosphere. The evaporative process then begins, thereby drawing sample into the distal end 63 of the capillary column 62. Assuming that the hydrodynamic flow rate resulting from the evaporation is known, the precise quantity of sample can be injected into the column 62 by allowing the evaporation to continue for the requisite period of time, and then stopping the evaporation by reimmersing the tip 70 in the buffer droplet.

Although the present invention has been disclosed in terms of a number of preferred embodiments, it will be understood that numerous variations and modifications could be made thereto without departing from the scope of the invention as defined by the following claims. For example, it should be understood that the use of the protective overcoating on the needle's contact layer could be employed with any type of ESI needle, and thus is not limited to use with the needle illustrated in FIG. 3. Similarly, although the system illustrated in FIG. 6 for preventing evaporation induced sampling errors is particularly useful in ultra-low flow rate CE interfaces, the system could be used with any other type of sample introduction system as well.

What is claimed is:

1. An electrospray ionization source comprising:
   a) a needle having an outer wall, a distal end and a tip end;
   b) a capillary located within said needle for supplying a sample solution from said distal end to said tip end;
   c) an electrical contact layer disposed on said outer wall adjacent said tip end; and
   d) an electrically insulating overcoating disposed on said electrical contact layer.

2. The apparatus of claim 1, wherein a ring portion of said electrical contact layer is exposed at said tip end.

3. The apparatus of claim 1, wherein said electrically insulating overcoating is formed from an oxide or a polymer.

4. The apparatus of claim 3, wherein said electrically insulating overcoating is formed from a mixture of SiO and $SiO_2$.

5. An electrospray ionization apparatus comprising:
   a) a capillary column for supplying a sample solution to an electrospray tip, said capillary column having a tip end and a distal end for receiving a sample; and
   b) means for preventing evaporative loss from said tip end during sample loading in said distal end.

6. The apparatus of claim 5, wherein said means for preventing evaporative loss further comprises means for blocking said tip end with a droplet of solution during sample loading.

7. The apparatus of claim 6, wherein said means for blocking said tip end with a droplet of solution further comprises:
   1) a tube having an open end positioned adjacent said tip end of said capillary column; and
   2) a droplet delivery device for retractably supplying a droplet of solution through said tube to said open end so that said droplet will block off said tip end of said capillary column.

8. The apparatus of claim 1, wherein said electrical contact layer is formed from gold.

9. The apparatus of claim 1, wherein said electrically insulating overcoating has a thickness of approximately 50 nm or less.

10. The apparatus of claim 1, wherein said electrical contact layer is formed from gold, and said electrically insulating overcoating is formed from an oxide or a polymer.

11. The apparatus of claim 10, wherein the thickness of said electrically insulating overcoating is approximately 50 nm or less.

12. The apparatus of claim 11, wherein said electrically insulating overcoating is formed from a mixture of SiO and $SiO_2$.

13. The apparatus of claim 12, wherein a ring portion of said electrical contact layer is exposed at said tip end.

14. The apparatus of claim 1, wherein said outer wall of said needle tapers to a sharp point at said tip and, and said capillary includes an elongated portion tapering slowly down to said tip end.

15. The apparatus of claim 14, wherein said outer wall has a thickness at said tip end of approximately 100 nm or less, and wherein said elongated portion extends to said tip end, said capillary being formed with an elongated, slowly tapering portion extending to said tip end from a point approximately 0.25–3.0 mm away from said tip end, said tapering portion having an inner diameter at said tip end of approximately 7 µm or less, and an inner diameter at said point approximately 0.25–3.0 mm away from said tip end of no greater than approximately 10 µm larger than said inner diameter at said tip end.

16. An electrospray ionization source comprising:
   a) a needle having a distal end, a tip end and an outer wall tapering to a sharp point at said tip end, said outer wall having a thickness at said tip end of approximately 100 nm or less; and
   b) a capillary located within said needle for supplying sample solution from said distal end to said tip end, said capillary including an elongated, slowly tapering portion extending to said tip end from a point approximately 0.25–3.0 mm away from said tip end, said tapering portion having an inner diameter at said tip end of approximately 7 µm or less, and an inner diameter at said point approximately 0.25–3.0 mm away from said tip end of no greater than 10 µm larger than said inner diameter at said tip end.

17. The apparatus of claim 16, wherein said needle is formed from fused silica which has been pulled and etched.

18. A method for making an ultra-low flow rate electrospray ionization source comprising the steps of:
   a) providing a capillary tube;
   b) pulling said tube to form a needle having a distal end and a tip end with a capillary connecting said distal end to said tip end, said capillary being formed with an elongated, slowly tapering portion extending to said tip end from a point approximately 0.25–3.0 mm away from said tip end, said tapering portion having an inner diameter at said tip end of approximately 7 µm or less, and an inner diameter at said point approximately 0.25–3.0 mm away from said tip end of no greater than approximately 10 µm larger than said inner diameter at said tip end; and
   c) etching said needle to form an outer wall tapering from said distal end to a sharp point at said tip end, the thickness of said outer wall at said tip end being approximately 100 nm or less.

* * * * *